(12) United States Patent
Toda

(10) Patent No.: US 6,366,675 B1
(45) Date of Patent: Apr. 2, 2002

(54) SOUND PRESSURE DETECTING SYSTEM

(76) Inventor: Kohji Toda, 1-49-18 Futaba, Yokosuka 239-0814 (JP)

( * ) Notice: Subject to any disclaimer, the term of this patent is extended or adjusted under 35 U.S.C. 154(b) by 0 days.

(21) Appl. No.: 09/317,082

(22) Filed: May 21, 1999

(51) Int. Cl.$^7$ .................. H04R 29/00; H04R 25/00; A61B 7/04; H01L 41/04
(52) U.S. Cl. .................. 381/56; 381/190; 381/191; 381/67; 381/150; 310/313 R; 310/313 B
(58) Field of Search .................. 381/56, 190, 150, 381/111, 114, 67, 173; 310/313 B, 313 R, 334

(56) References Cited

U.S. PATENT DOCUMENTS

| | | | | |
|---|---|---|---|---|
| 4,295,471 A | * | 10/1981 | Kaspari | 128/675 |
| 5,117,146 A | * | 5/1992 | Martin et al. | 310/313 R |
| 5,400,788 A | * | 3/1995 | Dias et al. | 128/662.03 |
| 6,142,948 A | * | 11/2000 | Toda | 600/459 |
| 6,195,440 B1 | * | 2/2001 | Warnaka et al. | 381/190 |

* cited by examiner

Primary Examiner—Forester W. Isen
Assistant Examiner—Laura A. Grier

(57) ABSTRACT

A sound pressure detecting system comprises a piezoelectric substrate, input and output interdigital transducers formed on an upper end surface of the piezoelectric substrate, a liquid cavity, an air cavity, a partition wall between the liquid cavity and the air cavity, a signal analyzing unit connected between the input- and output interdigital transducers, and a monitor. When an input electric signal is applied to the input interdigital transducer, a leaky elastic wave is excited in the piezoelectric substrate. The leaky elastic wave is radiated effectively in the form of a longitudinal wave into a liquid in the liquid cavity. The longitudinal wave is reflected at the partition wall, and then, is detected at the output interdigital transducer as a delayed electric signal. If the partition wall senses a sound pressure from the outside, the delay time of the delayed electric signal changes. Thus, the sound pressure is sensed from a change in the delayed electric signal at the signal analyzing unit, and displayed on the monitor.

6 Claims, 10 Drawing Sheets detecting assembly

SOUND PRESSURE DETECTING SYSTEM

BACKGROUND OF THE INVENTION

1. Field of the Invention

The present invention relates to a system for detecting a sound pressure by means of using a detecting assembly composed of a piezoelectric substrate and input- and output interdigital transducers.

2. Description of the Prior Art

Stethoscope is a typical one of conventional devices for detecting a sound pressure. When using a stethoscope, a sound pressure based on a heartbeat comes to one's ears directly, so that not only to have high-sensitive ears but also to be rich in experience are essential to check the heartbeat. It is difficult to remain a sound in the form of a document from an objective viewpoint, whether the sound is to be heard or not to be heard by one's ears. Moreover, it is impossible for stethoscope to transduce a sound pressure to an electric signal.

In general, it is under consideration to utilize a hydrophone for transducing a sound pressure to an electric signal, the hydrophone with a bulk wave type of piezoelectric vibrator operating in thickness mode. The hydrophone has some problems on sensitivity, limitation of operation frequencies, difficulty in use, resistance for a change of circumstances, resistance for noises, and so on. Thus, the hydrophone operating in thickness mode has difficulty in transducing a sound pressure to an electric signal.

SUMMARY OF THE INVENTION

An object of the present invention is to provide a sound pressure detecting system capable of sensing a sound with a high sensitivity, whether the sound is to be heard or not to be heard by one's ears.

Another object of the present invention is to provide a sound pressure (detecting system capable of operating in ultrasound.

Another object of the present invention is to provide a sound pressure detecting system capable of transducing a sound pressure to an electric signal and displaying the sound pressure on a monitor.

Another object of the present invention is to provide a sound pressure detecting system excellent in measurement accuracy, response time, durability, manufacturing, resistance for a change of circumstances, and resistance for noises.

A still other object of the present invention is to provide a sound pressure detecting system easy in use and having a small size which is very light in weight and has a simple structure.

According to one aspect of the present invention there is provided a sound pressure detecting system comprising a piezoelectric substrate, input- and output interdigital transducers formed on an upper end surface of the piezoelectric substrate, a liquid cavity, an air cavity, a partition wall between the liquid cavity and the air cavity, a signal analyzing unit connected between the input- and output interdigital transducers, and a monitor connected with the signal analyzing unit.

When an input electric signal is applied to the input interdigital transducer, a leaky elastic wave is excited in the piezoelectric substrate. The leaky elastic wave is radiated effectively in the form of a longitudinal wave into a liquid in the liquid cavity, the liquid being in contact with a lower end surface of the piezoelectric substrate. The partition wall reflects the longitudinal wave in the liquid. A reflected longitudinal wave is detected at the output interdigital transducer as a delayed electric signal. A sound pressure through the partition wall from the outside can be sensed by the signal analyzing unit with a high sensitivity in terms of a change in the delayed electric signal, and then, displayed on the monitor.

According to another aspect of the present invention there is provided a piezoelectric substrate made of a piezoelectric ceramic, the polarization axis thereof being parallel to the thickness direction thereof According to another aspect of the present invention there is provided a piezoelectric substrate made of a piezoelectric polymer film.

According to another aspect of the present invention there is provided a signal analyzing unit comprising a signal generator and a phase comparator. The signal generator generates the input electric signal. The phase comparator compares a phase of the input electric signal with that of the delayed electric signal, and senses the sound pressure in terms of a difference between the phase of the input electric signal and that of the delayed electric signal.

According to other aspect of the present invention there is provided a signal analyzing unit comprising an amplifier and a frequency counter. The amplifier amplifies the delayed electric signal, and delivers an amplified electric signal. The input interdigital transducer receives a part of the amplified electric signal as the input electric signal. Thus, the input- and output interdigital transducers and the amplifier form a delay-line oscillator. On the other hand, the frequency counter counts a frequency of the amplified electric signal, and senses the sound pressure in terms of a change in frequency of the amplified electric signal.

According to a further aspect of the present invention there is provided a signal analyzing unit comprising an amplifier and a frequency to voltage (F/V) converter. The amplifier amplifies the delayed electric signal, and delivers an amplified electric signal. The input interdigital transducer receives a part of the amplified electric signal as the input electric signal. Thus, the input- and output interdigital transducers and the amplifier form a delay-line oscillator. On the other hand, the F/V converter converts a frequency of the amplified electric signal into a voltage thereof, and senses the sound pressure in terms of a change in voltage of the F/V converted electric signal.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
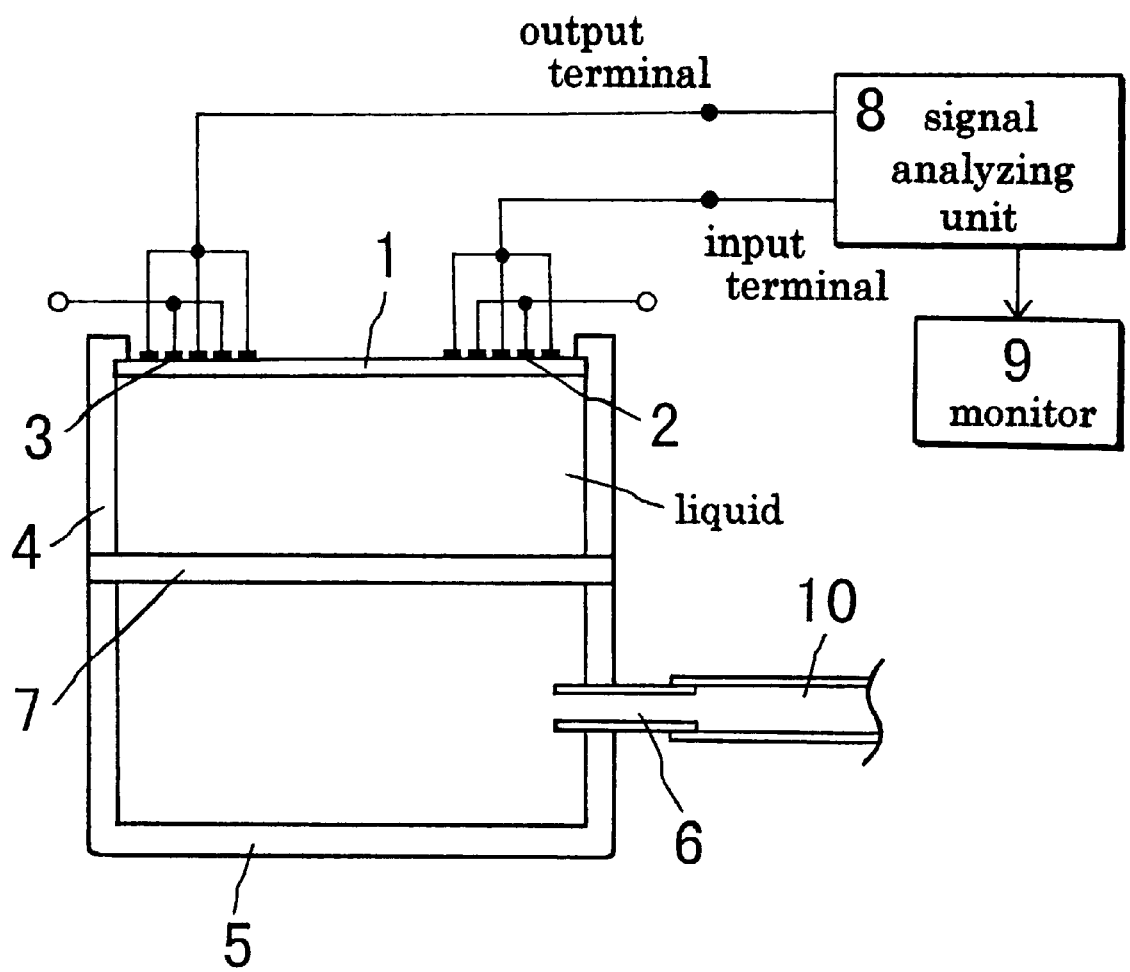
FIG. 1 shows a schematic illustration of a sound pressure detecting system according to an embodiment of the present invention.

FIG. 1 shows a schematic illustration of a sound pressure detecting system according to an embodiment of the present invention. The sound pressure detecting system comprises piezoelectric substrate 1 input interdigital transducer 2 having an input terminal, output interdigital transducer 3 having an output terminal, liquid cavity 4, air cavity 5 having aluminum pipe 6 for connecting the inside thereof and the outside, partition wall 7 between liquid cavity 4 and air cavity 5, a signal analyzing unit 8, and monitor 9. Piezoelectric substrate 1 is made of a ceramic thin plate or piezoelectric polymer film. Input interdigital transducer 2 and output interdigital transducer 3, having an arch-shape and made of an aluminum thin film, respectively, are formed on an upper end surface of piezoelectric substrate 1. A lower end surface of piezoelectric substrate 1 is in contact with a liquid in liquid cavity 4. It doesn't matter whether the liquid is viscous or not. Partition wall 7 is made of a nylon film having an elasticity and vibrating under sound pressure from the outside. Piezoelectric substrate 1, input interdigital transducer 2 and output interdigital transducer 3 form a detecting assembly. When sensing, for example, a heartbeat, polymer tube 10, made from nylon, silicone and so on, for transmitting a sound pressure from a stethoscope, is set at a terminal of aluminum pipe 6. Thus, the sound pressure detecting system in FIG. 1 has a small size which is very light in weight and has a simple structure.

Figure 2:
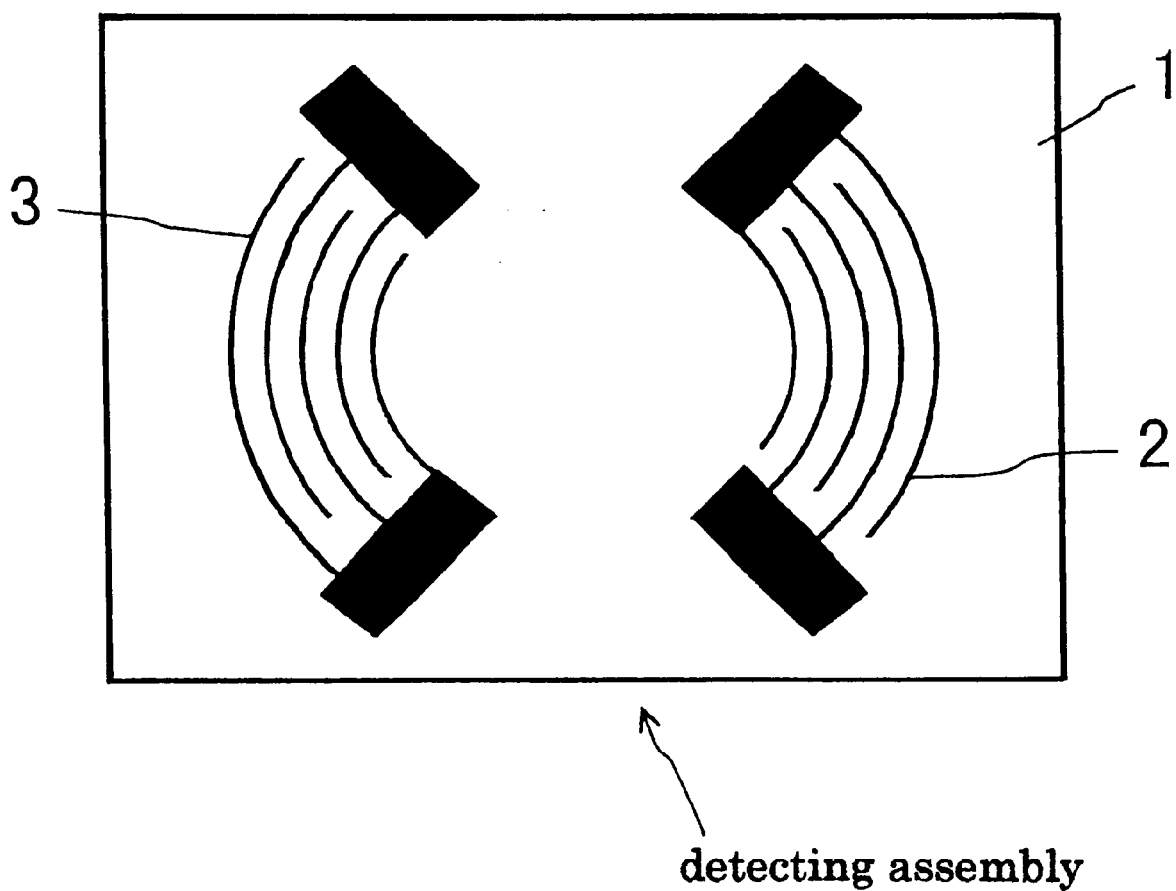
FIG. 2 shows a top plan view of the detecting assembly shown in FIG. 1.

FIG. 2 shows a top plan view of the detecting assembly shown in FIG. 1. The separation length between input interdigital transducer 2 and output interdigital transducer 3 is 6 mm. Input interdigital transducer 2 and output interdigital transducer 3 are arranged such that they make a pair with a concentric center, and have an aperture angle of 45°, an interdigital periodicity of 340 μm and 5 finger pairs, respectively.

Figure 8:
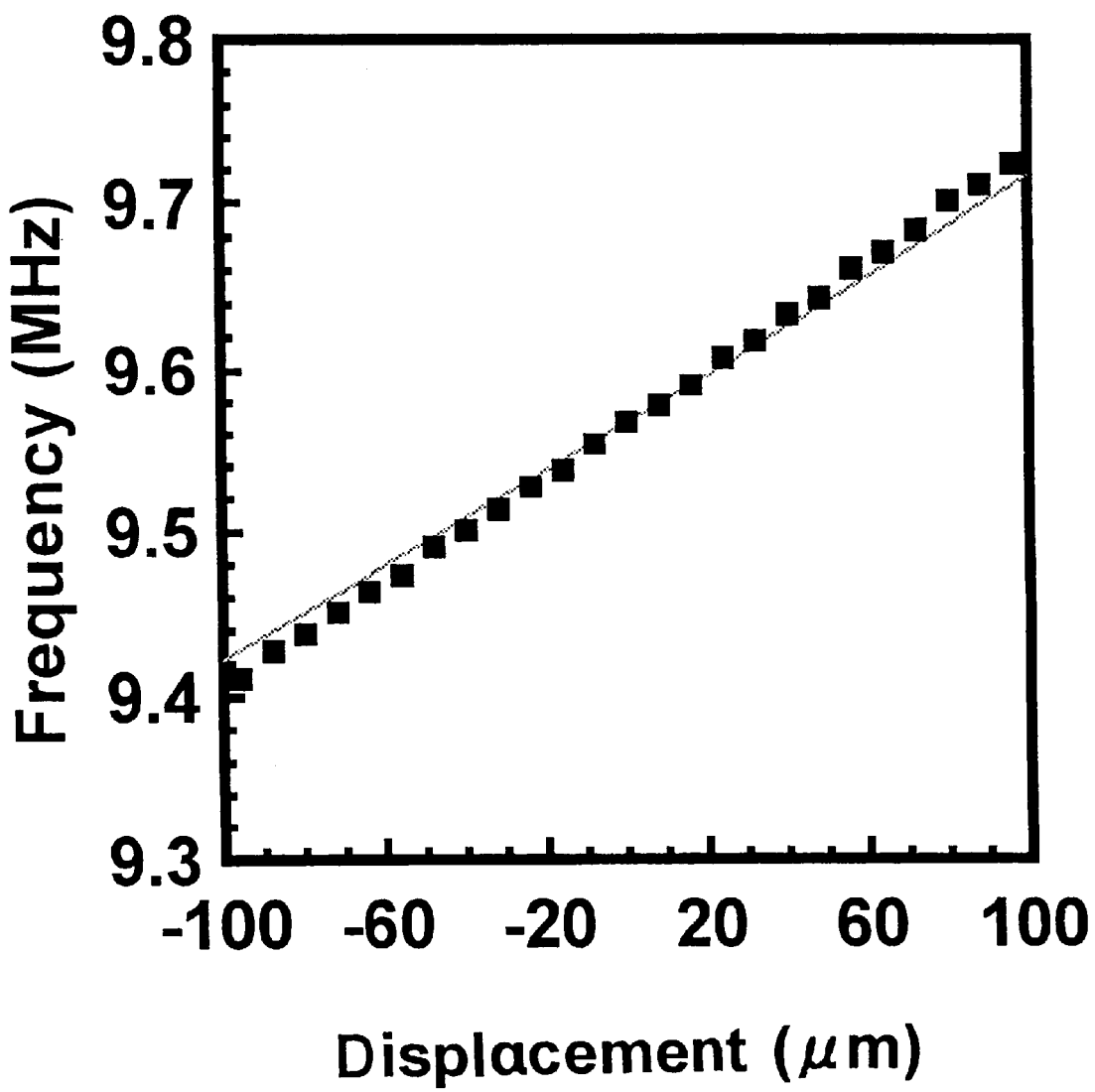
FIG. 8 shows a relationship between the frequency of the amplified electric signal, and the vibration displacement under sound pressure caused by an air flow into air cavity 5.

FIG. 8 shows a diagram of signal analyzing unit 8 according to a first embodiment. Signal analyzing unit 8 comprises signal generator 11, attenuator 12, phase shifter 13, and phase comparator 14.

Figure 3:
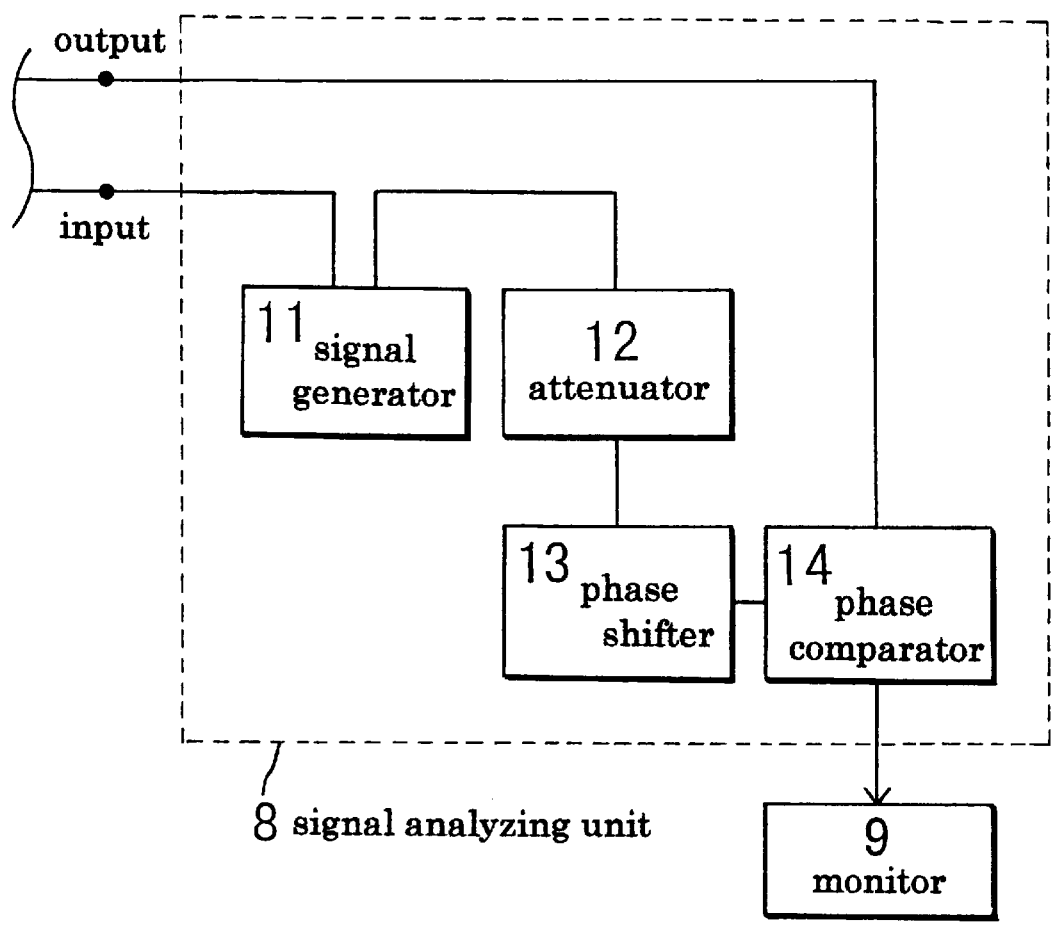
FIG. 3 shows a diagram of signal analyzing unit 8 according to a first embodiment.

In the sound pressure detecting system in FIG. 1 having signal analyzing unit 8 in FIG. 3, if an input electric signal, from signal generator 11, with a frequency approximately corresponding to the interdigital periodicity of input interdigital transducer 2, is applied to input interdigital transducer 2, a leaky elastic wave is excited in piezoelectric substrate 1. Because piezoelectric substrate 1 is made of a piezoelectric ceramic, and in addition, the polarization axis thereof is parallel to the thickness direction thereof, the leaky elastic wave is excited in piezoelectric substrate 1 effectively. The leaky elastic wave having the wavelength approximately equivalent to the interdigital periodicity is radiated effectively in the form of a longitudinal wave into the liquid, in other words, a mode conversion from the leaky elastic wave to the longitudinal wave in the liquid occurs. Such effective radiation is owing to the arch-shape of input interdigital transducer 2, which enables an ultrasound beam to go along a slant direction to the lower end surface of piezoelectric substrate 1. Partition wall 7, of which a top surface is approximately parallel to the lower end surface of piezoelectric substrate 1, reflects the longitudinal wave in the liquid. A reflected longitudinal wave is detected at output interdigital transducer 3 as a delayed electric signal with a frequency approximately corresponding to the interdigital periodicity. Such detection of the delayed electric signal is due to the arch-shape of output interdigital transducer 3, which can detect an ultrasound beam from a slant direction to the top surface of partition wall 7. A phase of the delayed electric signal is compared with that of the input electric signal at phase comparator 14. In this time, the phase of the input electric signal attenuated via attenuator 12, in case of sensing no sound pressure, is controlled to be coincident with that of the delayed electric signal by phase shifter 13.

Figure 4:
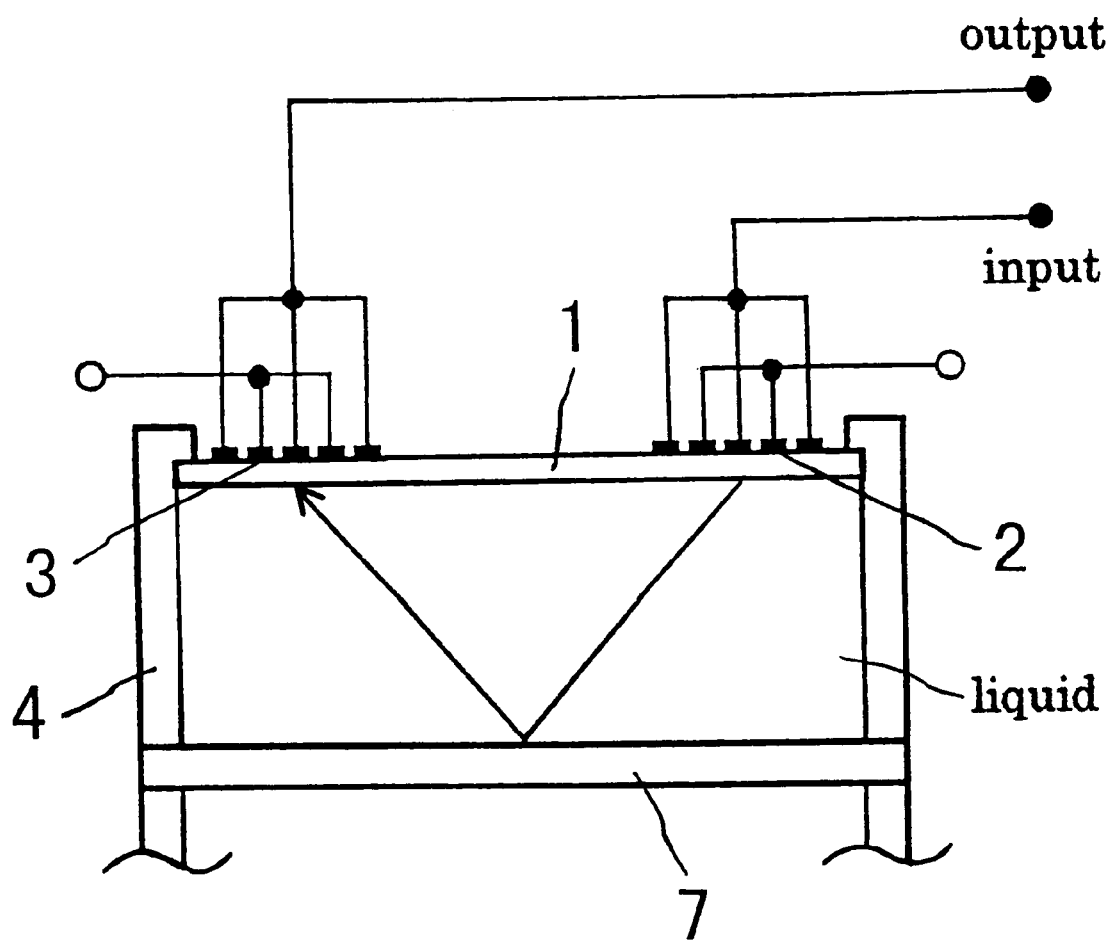
FIG. 4 shows an illustration exhibiting a path of the longitudinal wave traveling in the liquid by an arrow.
Figure 5:
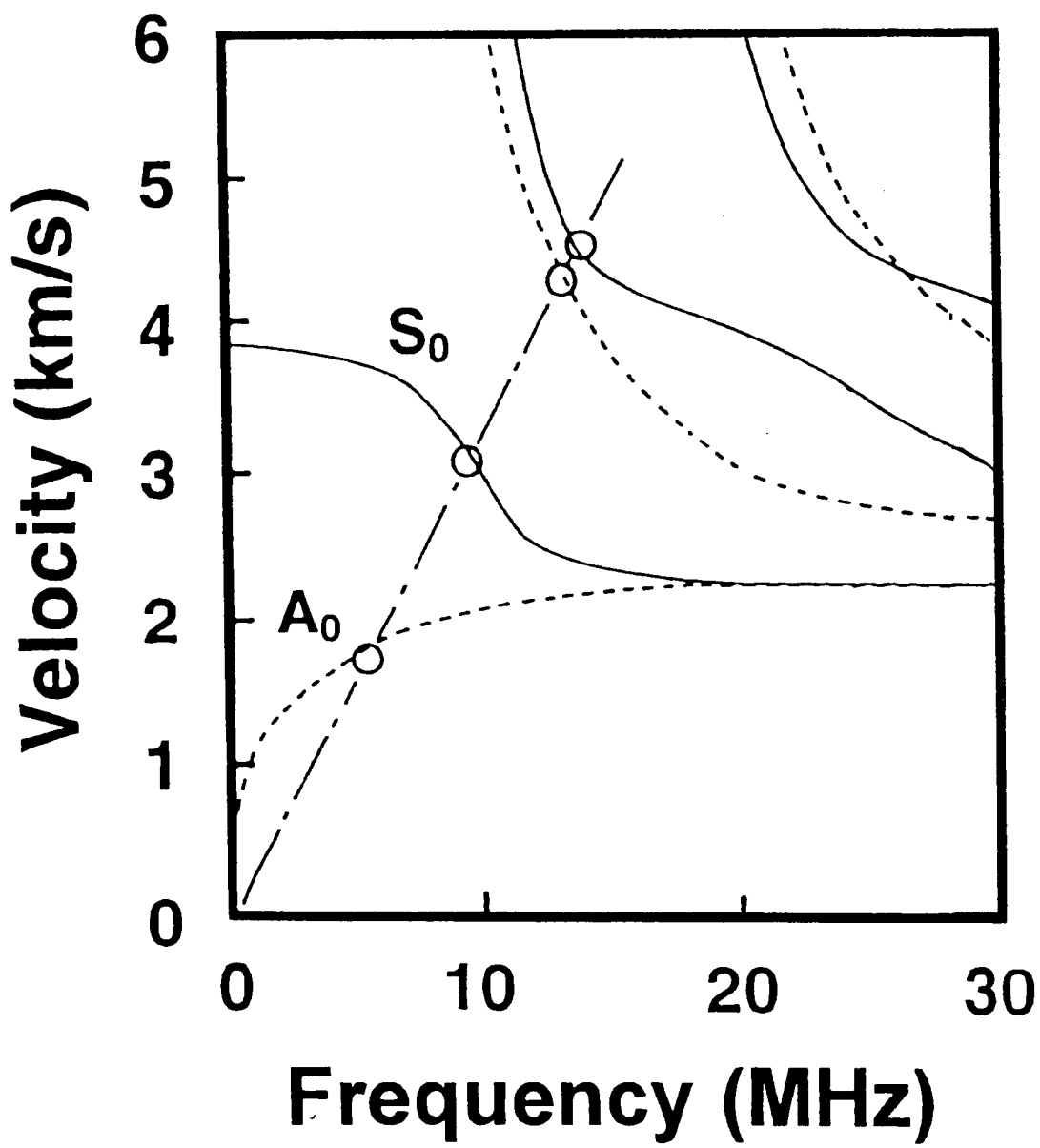
FIG. 5 shows a relationship between the frequency and the calculated phase velocity of a leaky elastic wave for each mode in piezoelectric substrate 1.

FIG. 4 shows an illustration exhibiting a path of the longitudinal wave traveling in the liquid by an arrow. If partition wall 7 senses a sound pressure from the outside, partition wall 7 is mechanically vibrated. As a result, a length of traveling path of the longitudinal wave is changed. A change in length of traveling path brings about a difference between a phase of the input electric signal and that of the delayed electric signal, Thus, a sound pressure through partition wall 7 can be sensed by signal analyzing unit 8 with a high sensitivity in terms of a phase difference, and then, displayed on monitor 9, FIG. 5 shows a relationship between the frequency and the calculated phase velocity of a leaky elastic wave for each mode in piezoelectric substrate 1. Piezoelectric substrate 1 has a shear wave velocity of 2,450 m/s and a longitudinal wave velocity of 4,390 m/s. Each mode has an effective radiation condition of the longitudinal wave into the liquid.

Figure 6:
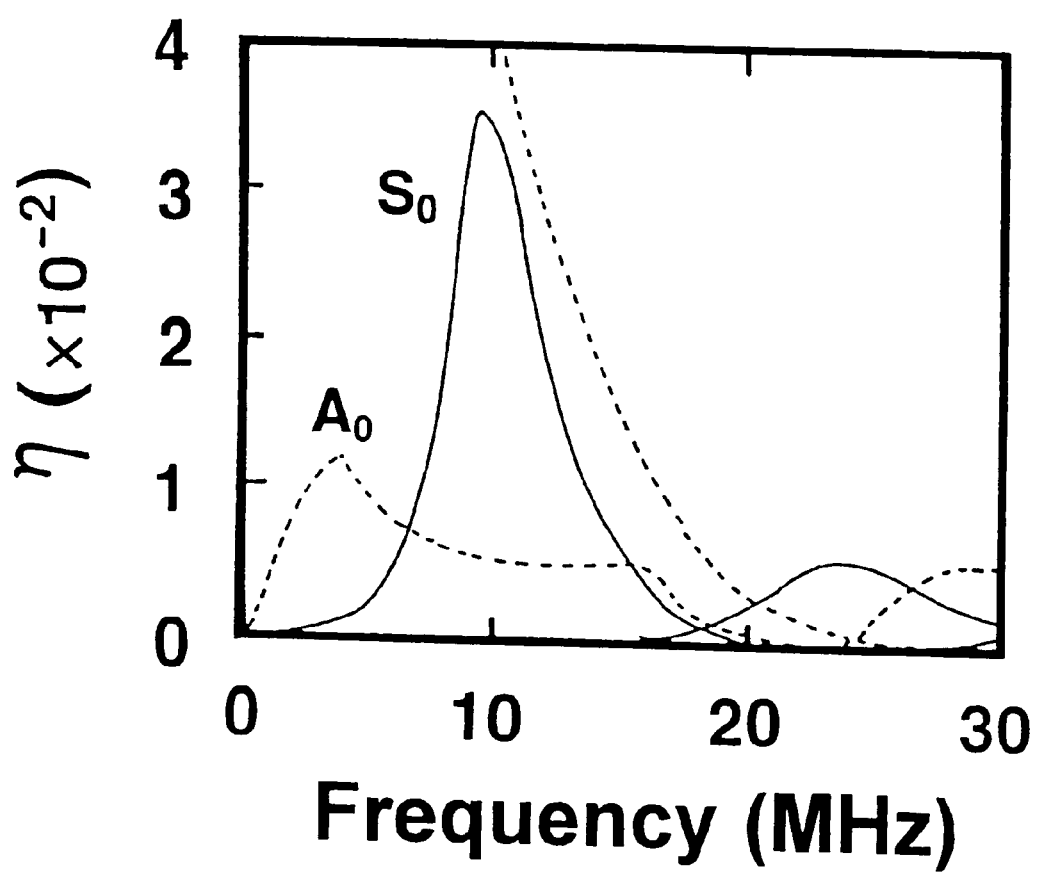
FIG. 6 shows a relationship between the frequency and the calculated transducer efficiency g for a longitudinal wave radiation into the liquid.

FIG. 6 shows a relationship between the frequency and the calculated transducer efficiency η for a longitudinal wave radiation into a liquid (water). It should be noted that the $S_0$ mode curve has the highest peak at around 9.5 MHz, that is the most appropriate operation frequency.

Figure 7:
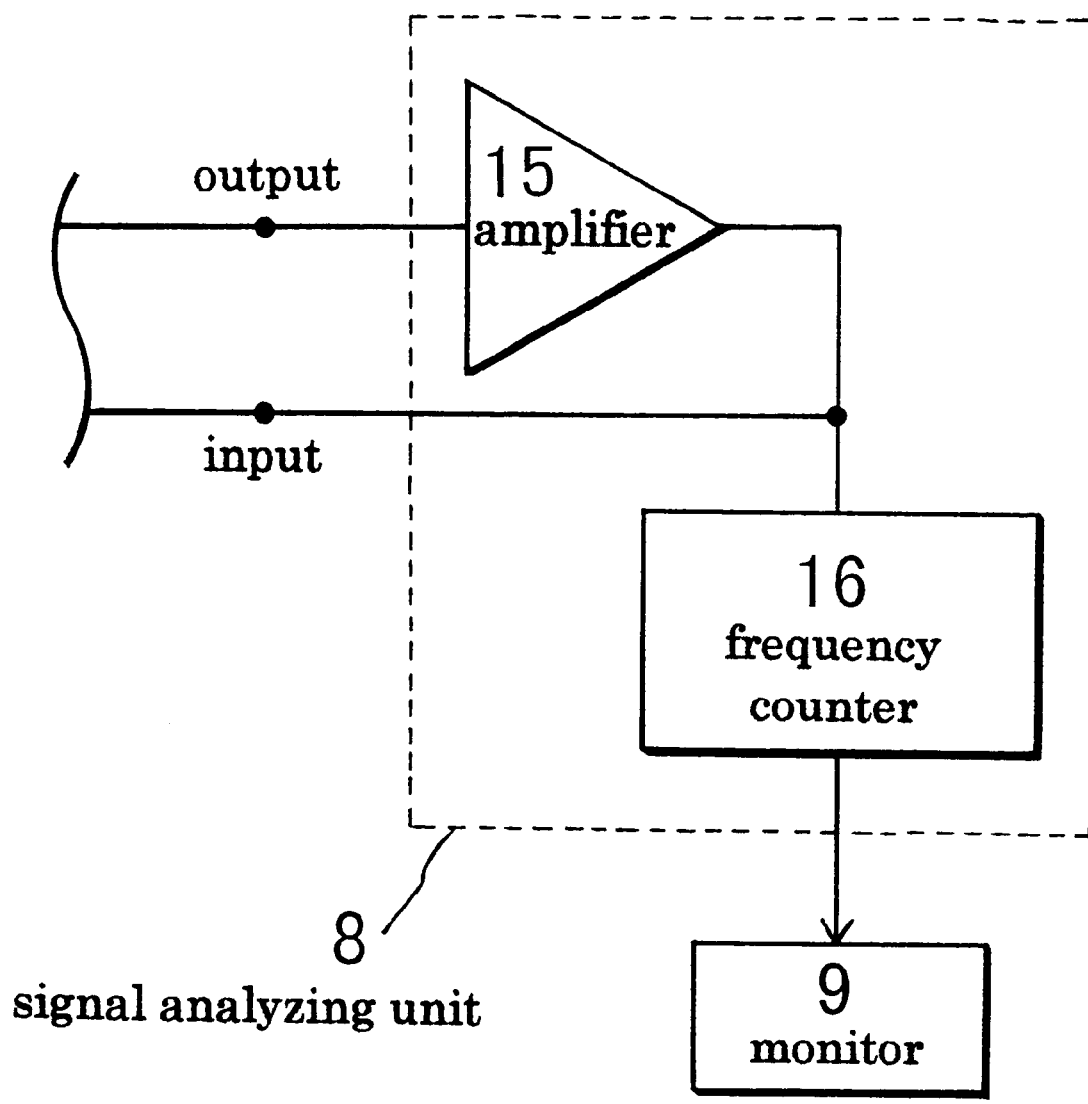
FIG. 7 shows a diagram of signal analyzing unit 8 according to a second embodiment.

FIG. 7 shows a diagram of signal analyzing unit 8 according to a second embodiment. Signal analyzing unit 8 comprises amplifier 15 and frequency counter 16.

In the sound pressure detecting system in FIG. 1 having signal analyzing unit 8 in FIG. 7, if an input electric signal is applied to input interdigital transducer 2, a leaky elastic wave is excited in piezoelectric substrate 1. The leaky elastic wave is radiated effectively in the form of a longitudinal wave into the liquid. The longitudinal wave reflected at partition wall 7 is detected at output interdigital transducer 3 as a delayed electric signal. The delayed electric signal is amplified via amplifier 15. A part of an amplified electric signal by amplifier 15 is applied to input interdigital transducer 2 again. Thus, input interdigital transducer 2, output interdigital transducer 3 and amplifier 15 form a self-oscillation type of delay-line oscillator. A remaining part of the amplified electric signal is transmitted to frequency counter 16. If partition wall 7 senses a sound pressure from the outside, a frequency of the amplified electric signal is changed. Therefore, a sound pressure through partition wall 7 can be sensed by signal analyzing unit 8 in terms of a change in frequency of the amplified electric signal, and then, displayed on monitor 9.

It is possible to sense a sound pressure caused by an air flow into air cavity 5. When an air flows into air cavity 5, partition wall 7 is mechanically vibrated, causing a variation in length of traveling path of the longitudinal wave in the liquid. Such a variation in length of traveling path is detected in terms of a change in frequency of the amplified electric signal.

FIG. 8 shows a relationship between the frequency of the amplified electric signal, and the vibration displacement under sound pressure caused by an air flow into air cavity 5. It is clear that the frequency is linearly correlated to the vibration displacement. Thus, it is possible to sense a sound pressure through partition wall 7 in terms of a frequency change.

Figure 9:
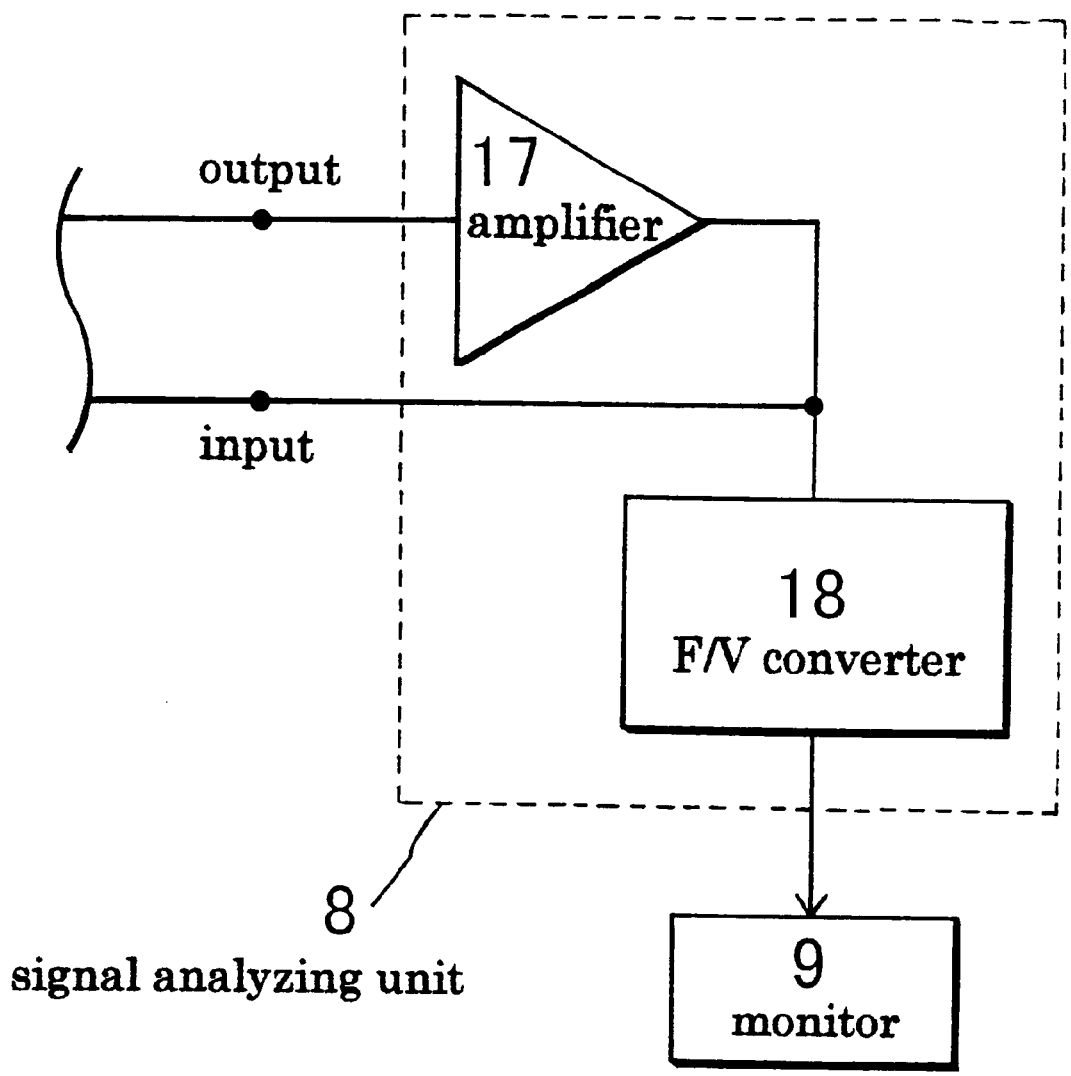
FIG. 9 shows a diagram of the signal analyzing unit 8 according to a third embodiment.

FIG. 9 shows a diagram of the signal analyzing unit 8 according to a third embodiment. Signal analyzing unit 9 comprises amplifier 17, and frequency to voltage (F/V) converter 18.

In the sound pressure detecting system in FIG. 1 having signal analyzing unit 8 in FIG. 9, if an input electric signal is applied to input interdigital transducer 2, a leaky elastic wave is excited in piezoelectric substrate 1. The leaky elastic wave is radiated effectively in the form of a longitudinal wave into the liquid. The longitudinal wave reflected at partition wall 7 is detected at output interdigital transducer 8 as a delayed electric signal. The delayed electric signal is amplified via amplifier 17. A part of an amplified electric signal by amplifier 17 is applied to input interdigital transducer 2 again. Thus, input interdigital transducer 2, output interdigital transducer 3 and amplifier 17 form a self-oscillation type delay-line oscillator. A remaining part of the amplified electric signal is transmitted to F/V converter 18. If partition wall 7 senses a sound pressure from the outside, a voltage of the F/V converted electric signal is changed. Therefore, a sound pressure through partition wall 7 can be sensed by signal analyzing unit 8 in terms of a change in voltage of the F/V converted electric signal, and then, displayed on monitor 9.

When sensing a heartbeat, a terminal part of a stethoscope is connected with polymer tube 10 set at the terminal of aluminum pipe 6. Thus, a sound pressure from the stethoscope is transmitted to partition wall 7 effectively.

Figure 10:
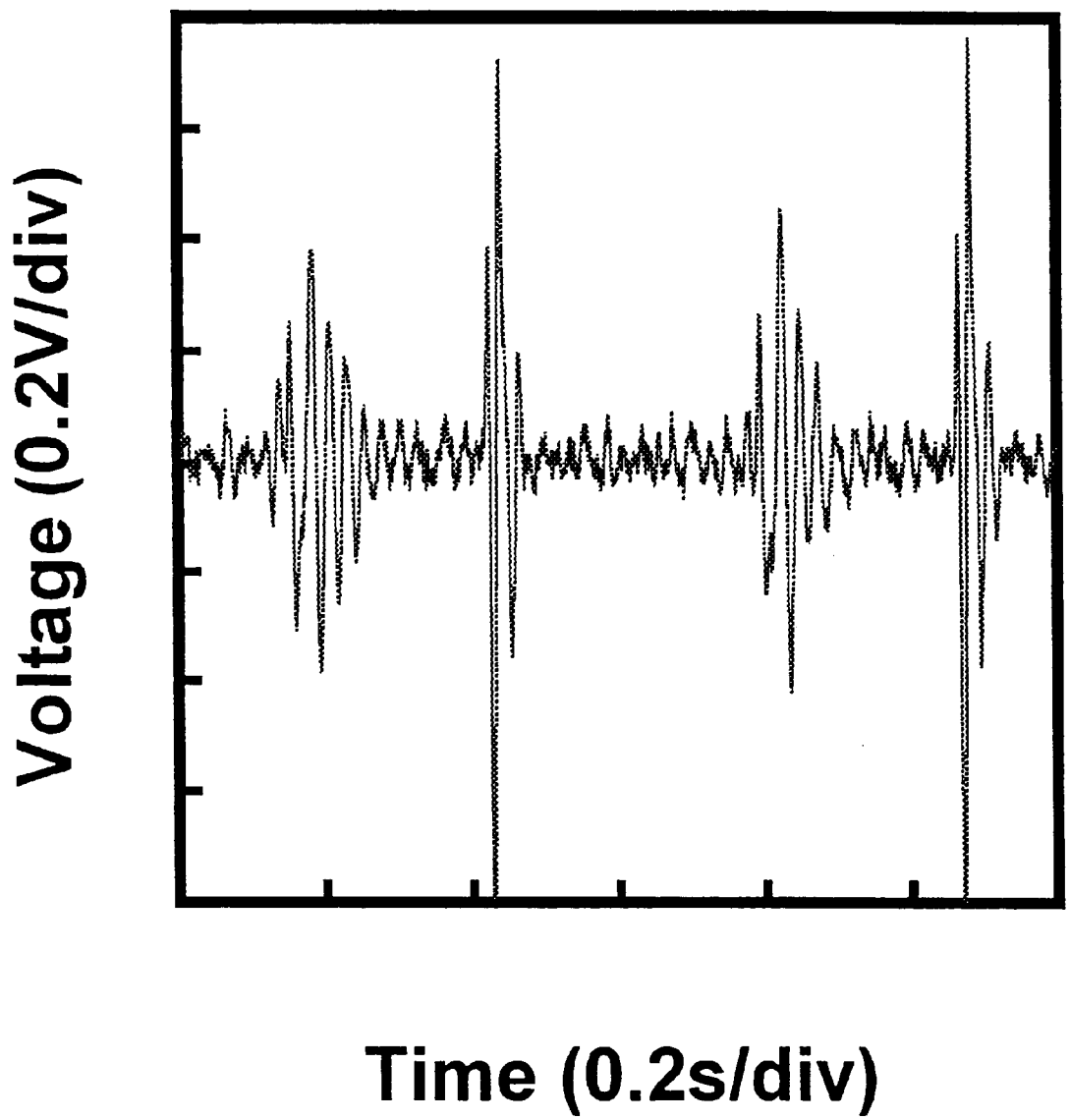
FIG. 10 shows a relationship between the voltage of the a F/V converted electric signal and time, in case of sensing a heartbeat.

FIG. 10 shows a relationship between the voltage of the F/V converted electric signal and time, in case of sensing a heartbeat. It is noted that a regular repetition in heartbeat is observed in terms of a change in voltage of the F/V converted electric signal.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims,

What is claimed is:

1. A sound pressure detecting system comprising:

a piezoelectric substrate having an upper- and a lower end surfaces being parallel to each other;

an input interdigital transducer having an arch-shape and formed on said upper end surface of said piezoelectric substrate, the thickness of said piezoelectric substrate being smaller than an interdigital periodicity of said input interdigital transducer;

an output interdigital transducer having an arch-shape and formed on said upper end surface of said piezoelectric substrate, said input- and output interdigital transducers making a pair with a concentric center;

a liquid cavity having a liquid in contact with said lower end surface of said piezoelectric substrate;

an air cavity;

a partition wall between said liquid cavity and said air cavity, said partition wall being made of a polymer film with elasticity;

a signal analyzing unit connected between said input- and output interdigital transducers: and a monitor connected with said signal analyzing unit, said piezoelectric substrate, and said input- and output interdigital transducers forming a detecting assembly, said input interdigital transducer receiving an input electric signal with a frequency approximately corresponding to said interdigital periodicity, exciting a leaky elastic wave in said piezoelectric substrate, and causing a mode conversion from said leaky elastic wave, having the wavelength approximately equivalent to said interdigital periodicity, to a longitudinal wave in said liquid, said partition wall reflecting said longitudinal wave, said output interdigital transducer detecting a reflected longitudinal wave as a delayed electric signal with a frequency approximately corresponding to said interdigital periodicity, said signal analyzing unit sensing a sound pressure through said partition wall via said air cavity in terms of a change in said delayed electric signal, and said monitor displaying said sound pressure.

2. A sound pressure detecting system as defined in claim 1, wherein said piezoelectric substrate is made of a piezoelectric ceramic, the polarization axis thereof being parallel to the thickness direction thereof.

3. A sound pressure detecting system as defined in claim 1, wherein said piezoelectric substrate is made of a piezoelectric polymer film.

4. A sound pressure detecting system as defined in claim 1, wherein said signal analyzing unit comprising:

a signal generator generating said input electric signal, and a phase comparator comparing a phase of said input electric signal with that of said delayed electric signal, and sensing said sound pressure in terms of a difference between said phase of said input electric signal and that of said delayed electric signal.

5. A sound pressure detecting system as defined in claim 1, wherein said signal analyzing unit comprising:

an amplifier amplifying said delayed electric signal and delivering an amplified electric signal, said input interdigital transducer receiving a part of said amplified electric signal as said input electric signal, said input- and output interdigital transducers and said amplifier forming a delay-line oscillator, and a frequency counter counting a frequency of said amplified electric signal, and sensing said sound pressure in terms of a change in frequency of said amplified electric signal.

6. A sound pressure detecting system as defined in claim 1, wherein said signal analyzing unit comprising:

an amplifier amplifying said delayed electric signal and delivering an amplified electric signal, said input interdigital transducer receiving a part of said amplified electric signal as said input electric signal, said input- and output interdigital transducers and said amplifier forming a delay-line oscillator, and a frequency to voltage converter converting a frequency of said amplified electric signal into a voltage thereof, and sensing said sound pressure in terms of a change in voltage of the converted electric signal by said converter.

* * * * *